(12) United States Patent
Vermeulen et al.

(10) Patent No.: US 7,811,232 B1
(45) Date of Patent: Oct. 12, 2010

(54) SYSTEM FOR CHARACTERIZING SKIN CONDITION

(75) Inventors: J. Dirk Vermeulen, Grand Rapids, MI (US); John D. Vermeulen, Grand Rapids, MI (US); William Dommer, Lowell, MI (US)

(73) Assignee: Chameleon Development LLC, Grand Rapids, MI (US)

( * ) Notice: Subject to any disclaimer, the term of this patent is extended or adjusted under 35 U.S.C. 154(b) by 0 days.

(21) Appl. No.: 11/867,973

(22) Filed: Oct. 5, 2007

Related U.S. Application Data (62) Division of application No. 10/709,183, filed on Apr. 20, 2004.

(60) Provisional application No. 60/320,126, filed on Apr. 21, 2003.

(51) Int. Cl.
*A61B 5/00* (2006.01)

(52) U.S. Cl. ........................................ 600/306; 424/9.8

(58) Field of Classification Search .................. 424/9.8; 600/306
See application file for complete search history.

(56) References Cited

U.S. PATENT DOCUMENTS

| | | | |
|---|---|---|---|
| 3,993,742 A | 11/1976 | Rey et al. | |
| 4,313,393 A | 2/1982 | Barbuscio et al. | |
| 4,532,937 A | 8/1985 | Miller | |
| 4,820,518 A * | 4/1989 | Murphy et al. | 424/401 |
| 4,981,145 A | 1/1991 | Goldstein | |
| 5,088,502 A | 2/1992 | Miller | |
| 5,094,248 A | 3/1992 | Kawam | |
| 5,119,828 A | 6/1992 | Miller | |
| 5,433,214 A | 7/1995 | Brehm et al. | |
| 5,534,267 A * | 7/1996 | Neunhoeffer et al. | 424/701 |
| 5,720,942 A * | 2/1998 | Johnson | 424/59 |
| 6,150,403 A | 11/2000 | Biedermann et al. | |
| 6,309,655 B1 * | 10/2001 | Minnix | 424/401 |
| 6,316,021 B1 | 11/2001 | Gueret | |
| 6,365,363 B1 | 4/2002 | Parfenov et al. | |
| 6,733,766 B2 | 5/2004 | Gott et al. | |
| 2003/0004404 A1 | 1/2003 | Subramanyan et al. | |
| 2003/0108542 A1* | 6/2003 | Pruche et al. | 424/130.1 |
| 2003/0171247 A1 | 9/2003 | Meine et al. | |
| 2004/0067890 A1 | 4/2004 | Gupta | |

FOREIGN PATENT DOCUMENTS

| | | | | |
|---|---|---|---|---|
| JP | 56025106 A | * | 3/1981 | |
| JP | 56081522 A | * | 7/1981 | |

OTHER PUBLICATIONS

English translation of abstract of JP 56-081522.*
English translation of JP 56-081522 to Fukuyama et al., translated Aug. 2009.*

\* cited by examiner

*Primary Examiner*—Patricia C Mallari
(74) *Attorney, Agent, or Firm*—Barnes & Thornburg LLP (57) ABSTRACT

A system for characterizing skin condition comprises a spreadable indicator and a reference. The indicator is suitable for application to human skin and visually changeable when in contact with the oil on human skin. The visual change of the indicator is representative of the amount of the oil in contact with the indicator. The reference relates a plurality of possible visual changes of the indicator to a plurality of skin conditions, whereby a user can compare the reference to the visual change of the indicator to characterize a skin condition of human skin due to the amount of the oil on the human skin in contact with the indicator.

13 Claims, 10 Drawing Sheets

SYSTEM FOR CHARACTERIZING SKIN CONDITION

CROSS-REFERENCE TO RELATED APPLICATIONS

This application is a division of U.S. patent application Ser. No. 10/709,183, filed Apr. 20, 2004, which claims the benefit of U.S. Provisional Patent Application No. 60/320,126, filed Apr. 21, 2003, which are both incorporated herein by reference in their entirety.

BACKGROUND OF THE INVENTION

1. Field of the Invention

The invention relates to a system for characterizing skin condition.

2. Description of Related Art

Human skin secretes oil, most noticeably on the face and scalp, to prevent water loss from the skin surface and protect the skin against infection by bacteria and fungi. Skin oil is a complex mixture of sebum, lipids from the surface skin cells, sweat, and environmental material. Sebum, a variable mixture of lipids produced by sebaceous glands in the skin, contains mostly glycerides and free fatty acids in addition to wax esters, squalene, cholesterol esters, and cholesterol. While most of the sebaceous glands open out into the hair follicle, some open directly onto the skin surface. Because sebum constitutes a significant portion of skin oil, some people generically use the term "sebum" to describe all skin oil; however, technically sebum is only one of the oily substances on the surface of the skin.

The rate at which oil is produced and secreted to the surface of the skin varies greatly from person to person. Because androgens, commonly referred to as sex hormones, regulate sebum production, the quantity and distribution of sebum varies with sex and age and can be altered by disease and medications. Additionally, seasonal and environmental changes can significantly impact the amount of sebum present on the skin's surface.

Facial cosmetics and beauty products are formulated for use with distinct skin types, but it is often challenging to visually determine the skin condition of the face. As a result, the selection of appropriate facial cosmetics is often arbitrary, sometimes difficult, and often costly. Furthermore, the amount of sebum secreted to the skin's surface is not constant across the many areas of the face due to the increased size and number of sebaceous glands on the forehead and chin. This makes the selection and application of suitable facial products even more problematical.

Systems have been developed to quantify oil production and characterize skin type. For example, U.S. Pat. No. 4,313,393 to Barbuscio et al. describes an indicating device with a sheet material treated with an oil-soluble dye surrounded by a transparent permeable membrane. The strip is applied to a certain area on the hair or scalp, and skin oil present in the area permeates the membrane and is absorbed by the dye-treated material. As the oil contacts and solubilizes the dye, a visual color change occurs. A standardized comparison chart is used to assess the degree of oil in the tested area of the hair/scalp. In U.S. Pat. No. 4,981,145 to Goldstein, a sampling device with absorbent sheets is attached to the facial skin surface with a headband for a predetermined period of time, approximately 3 hours. After removal, the device is folded, sealed, and mailed to a test laboratory where skin oil content is determined by weighing methods.

Other systems are based on the fact that skin oil deposited on a translucent element causes that element to become transparent. For example, U.S. Pat. No. 5,094,248 to Kawam describes a translucent microporous polymeric film that absorbs and retains oil when applied to the skin manually or with a professional device for 5-30 seconds. The used film is positioned in front of a dark background to create a pattern through the transparent areas, and the pattern is compared to several references for skin type characterization.

The devices and systems developed thus far have been deficient in several aspects. The tape or sheet systems have a small surface area relative to the size of the face and, therefore, they only measure the oiliness for the specific area to which the tape is applied. In addition, these laminar-type systems are difficult to apply evenly and with consistent skin contact over the contours of an item with complex topography such as the human face. As discussed above, insufficient information regarding the entire face could lead to application of inappropriate facial products. Additionally, the devices cannot be confidently self-administered; either a professional is required to apply the system or special meters or equipment are needed to determine the results.

SUMMARY OF THE INVENTION

A system according to one embodiment of the invention for characterizing skin condition comprises a spreadable indicator suitable for application to human skin and visually changeable when in contact with the oil on human skin, wherein the visual change of the indicator is representative of the amount of the oil in contact with the indicator; and a reference relating a plurality of possible visual changes of the indicator to a plurality of skin conditions, whereby a user can compare the reference to the visual change of the indicator to characterize a skin condition of human skin due to the amount of the oil on the human skin in contact with the indicator.

The spreadable indicator can be a facial mask, such as a clay-based mask or a polymer-based mask. The spreadable indicator can be a gel. The spreadable indicator can be a powder.

The indicator can comprise at least one dye soluble with oil found on human skin to effect the visual change of the indicator. The at least one dye can comprise at least one Drug and Cosmetics colorant from the group consisting of violet 2, yellow 11, and red 17.

The visual change can be at least one of an appearance of a color and a change in intensity of a color.

The reference can comprise indicia representative of the plurality of possible visual changes of the indicator. The indicia can comprise a color chart.

The reference can assists in selecting cosmetics appropriate for the characterized skin condition.

The indicator can be in the form of a pressed powder. The indicator can be in the form of a loose powder.

The system can further comprise an applicator configured to apply the indicator to the human skin. The applicator can comprise at least one of a sponge, a pad, a puff, and a brush.

DESCRIPTION OF THE PREFERRED EMBODIMENTS

The present invention allows a user to determine the user's skin condition over a surface area of the user's body, such as the face, including various regions of differing skin condition, such as oily, normal, or dry. The invention facilitates selection of cosmetics and beauty products formulated for use with detected distinct skin conditions; the selection of these products being simpler due to knowledge of the skin condition and location of the user's varying skin conditions. In one aspect, the invention relates to a visual characterization of the quantity of skin oil present on various areas of the skin's surface, which can vary greatly from person to person and is dependent on several biological and environmental factors that frequently change with time. The present invention provides a skin type indicator and method that can be self-administered, self-interpreted, and employed repeatedly.

Figure 1:
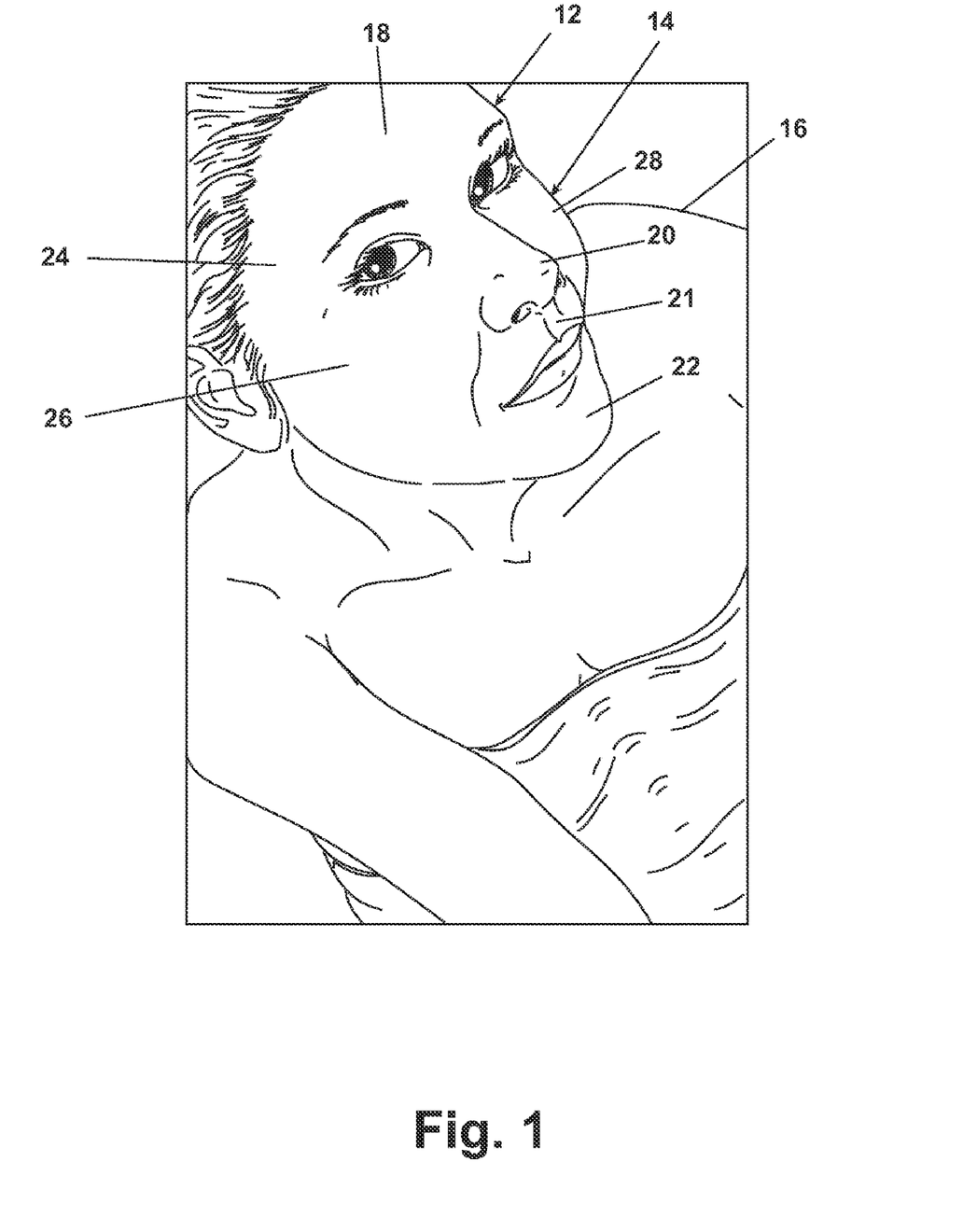
FIG. 1 is a perspective view of a user's upper body and face prior to application of an indicator according to the invention.
Figure 2:
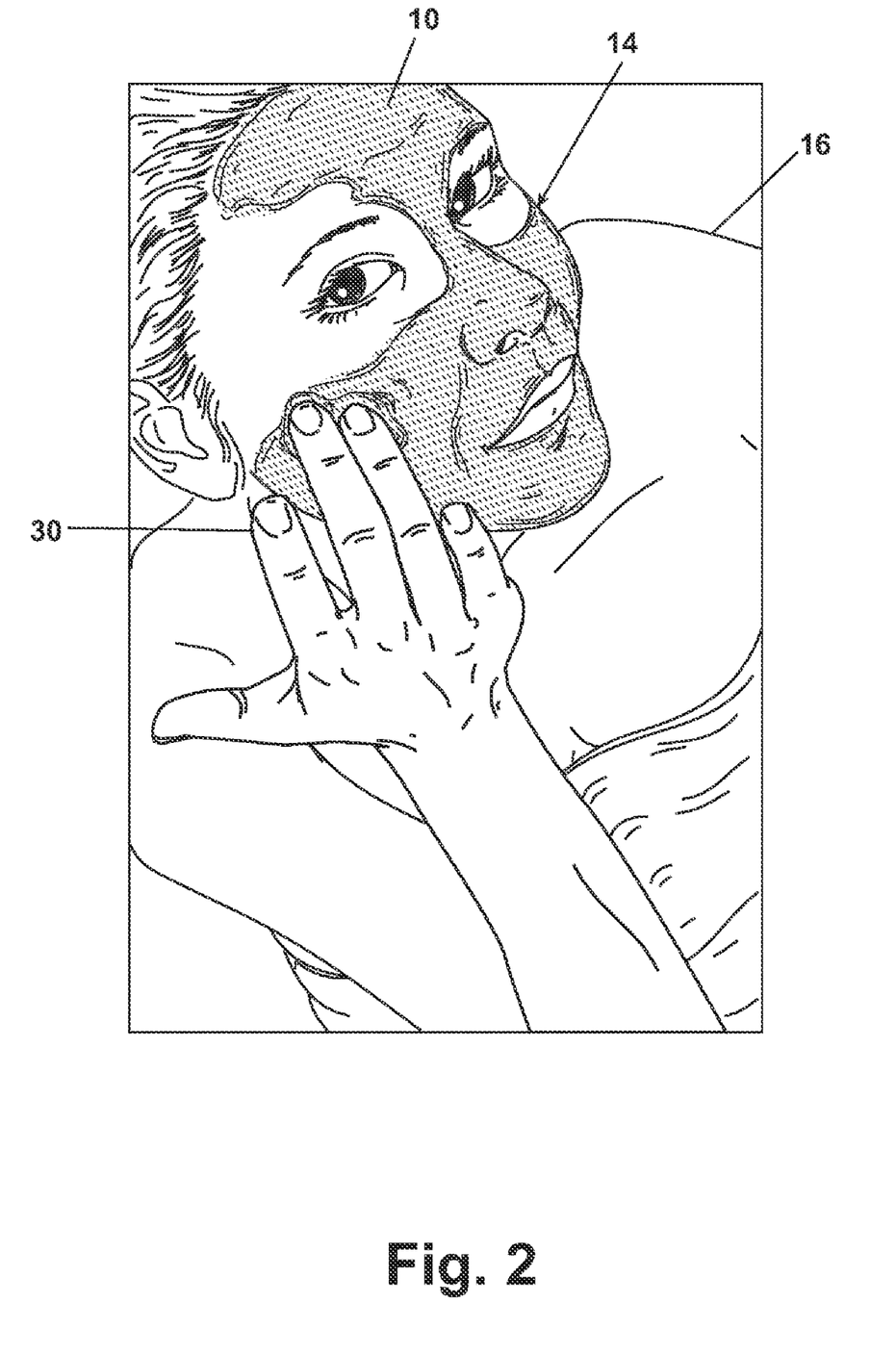
FIG. 2 is a perspective view of the user in FIG. 1 applying a spreadable form of the indicator by hand.

With reference to the drawings, and to FIGS. 1-4 in particular, the present invention comprises a skin condition indicator 10 that provides a visual indication of a user's skin condition. In FIG. 2, the indicator 10 is shown in a spreadable form, such as a spreadable mask. According to the invention, a "mask" includes any type of substance that can be directly applied to desired area(s) of a user's body. The spreadable form can be, for example, a ceramic-based indicator, such as a clay indicator, a polymer-based indicator, such as a gel indicator or a peelable indicator, or any other suitable system that can be spread over the desired areas of the user's body. However, the indicator 10 is not limited to a spreadable form and can assume many forms in addition to the aforementioned spreadable form. As an example, the indicator 10 can be a powder or a low viscosity fluid. The viscosity of the low viscosity fluid is preferably comparable to the viscosity of water. The spreadable form, the powder form, and the low viscosity fluid form are all flowable and conform to contours of the user's body.

Referring now to FIG. 1, a face 14 and an upper body 16 of a user 12 are shown. The face 14 includes well-known facial areas, such as a forehead 18, a nose 20, an upper lip 21, a chin 22, a temple 24, a right cheek 26, and a left cheek 28, each of which can have varying degrees of sebum secretion and, thus skin oil and skin conditions across the topography of the face 14. As shown in FIG. 2, the user 12 can apply the indicator 10 to the entire face 14 or to desired areas of the face 14. By way of example, the user 12 can apply the indicator 10 by hand 30 in a well-known manner. For example, when the indicator 10 is spreadable, the user 12 can accumulate a volume of the indicator 10 on the user's hand 30 and spread the indicator 10 over the topography of the face 12, taking care to avoid depositing any volume of the indicator 10 into sensitive areas such as the eyes, nose, and mouth as well as to avoid inadvertently spreading the indicator 10 into areas where the indicator 10 would be difficult to remove, such as the user's hair. Prior to applying the indicator 10 with the hand 30, the user 12 preferably washes the hand 30 or applies an oil barrier, such as a glove. Other methods and systems for applying the indicator 10 are described hereinafter.

Figure 3:
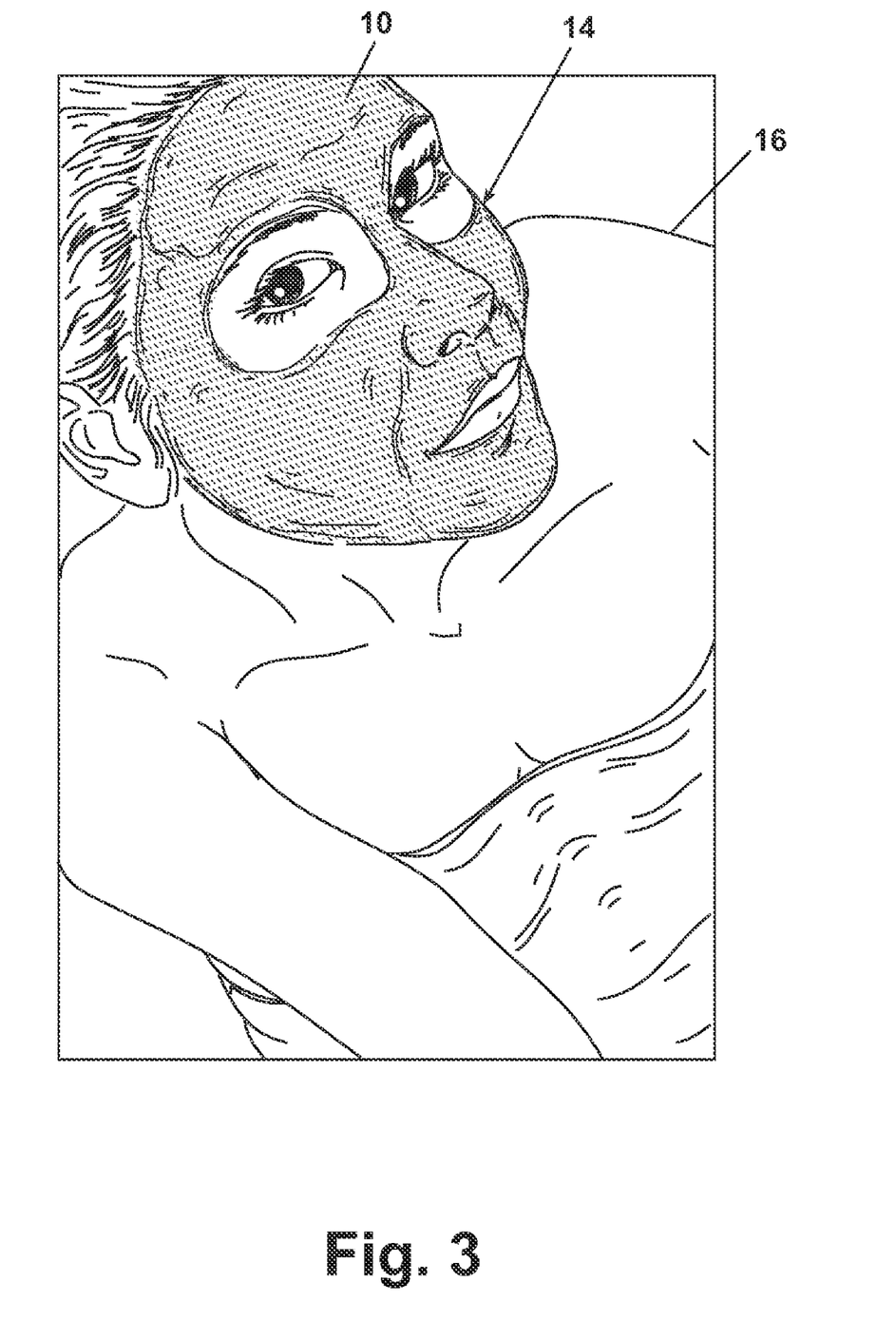
FIG. 3 is a perspective view of the user in FIG. 1 with the applied indicator shown in an inactivated state and the user shown waiting for the applied indicator to activate.

Once the indicator 10 has been applied to the desired area or areas of the face 14, the user 12 waits a suitable length of time for the indicator 10 to activate, as indicated in FIG. 3. Activation occurs when the indicator 10 has contacted a sufficient amount of natural substance on the surface of the skin, such as skin oil, to cause the ingredients in the indicator 10 responsible for the visual indication of the skin's condition to react and display the accurate visual indication. While it could be said that the user 12 should wait for the indicator 14 to "dry", full dryness is not a prerequisite for the indicator 10. A user 12 need only wait a sufficient time for the indicator 10 to activate, i.e. show a visual representation of the user's skin condition, normally when an agent in the indicator 10 (as described hereinafter) completely reacts with one or more available substances secreted from the skin. The time required for activation can vary according to the type of the indicator 10, the amount of the indicator 10 applied to the skin, and the characteristics of the skin. The activation initiates adjacent the skin and progresses outward through the indicator 10. When the activation reaches the outer surface of the indicator 10, it becomes visible to the user 12. Hence, the indicator 10 is preferably applied in a layer having a thickness that corresponds to a desired activation time and an optimized performance.

It will be understood that, although the invention is described herein with respect to use on facial areas, the indicator 10, according to the invention, can be used on all areas of the human body without departing from the scope of this invention. Description of the indicator 10 in conjunction with the face 14 of the user 12 shall be interpreted by way of example, not of limitation. The invention is suitable for use on all areas of the body and for detection of skin condition on all areas of the body. It has been found, by way of describing a preferred embodiment, that the invention is particularly useful in selection of cosmetics, which are predominantly used on the facial area of the body.

Figure 4:
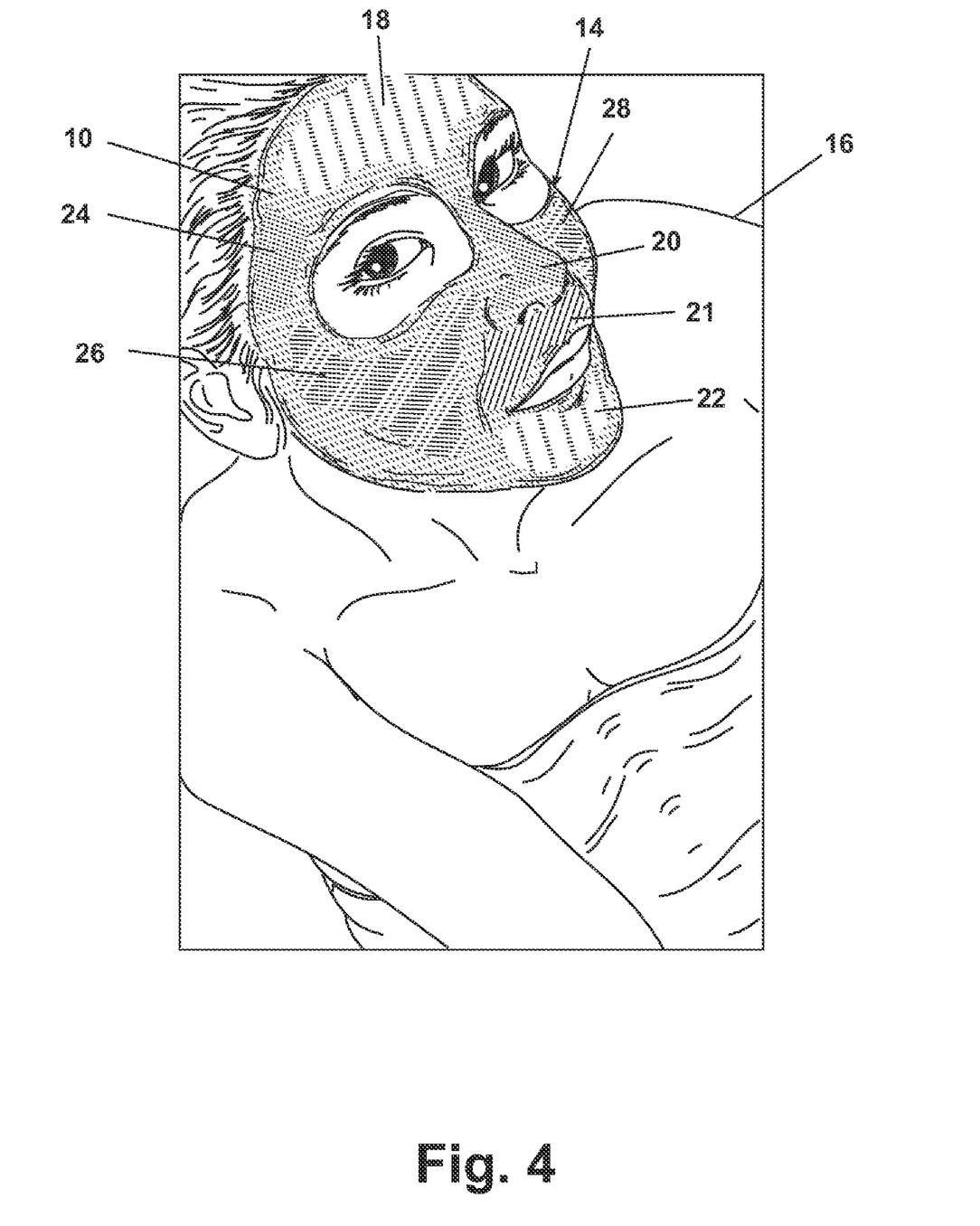
FIG. 4 is a perspective view of the user in FIG. 1 having the activated indicator, wherein the indicator displays a visual indication according to the amount of skin oil contacted.

As the indicator 10 activates, it provides a visual indication, such as a color change, based on the concentration of oil present of the areas of the face 14 to which it was applied, as seen in FIG. 4. A reference 32 can be used in conjunction with the indicator 10 to assist the user 12 in assessing skin condition by providing a visual reference by which the user 12 can compare the visual indications on the activated indicator 10 with a corresponding visual indication on the reference 32. In one aspect, the reference 32 comprises a color chart (also referred to with reference numeral 32).

Figure 5:
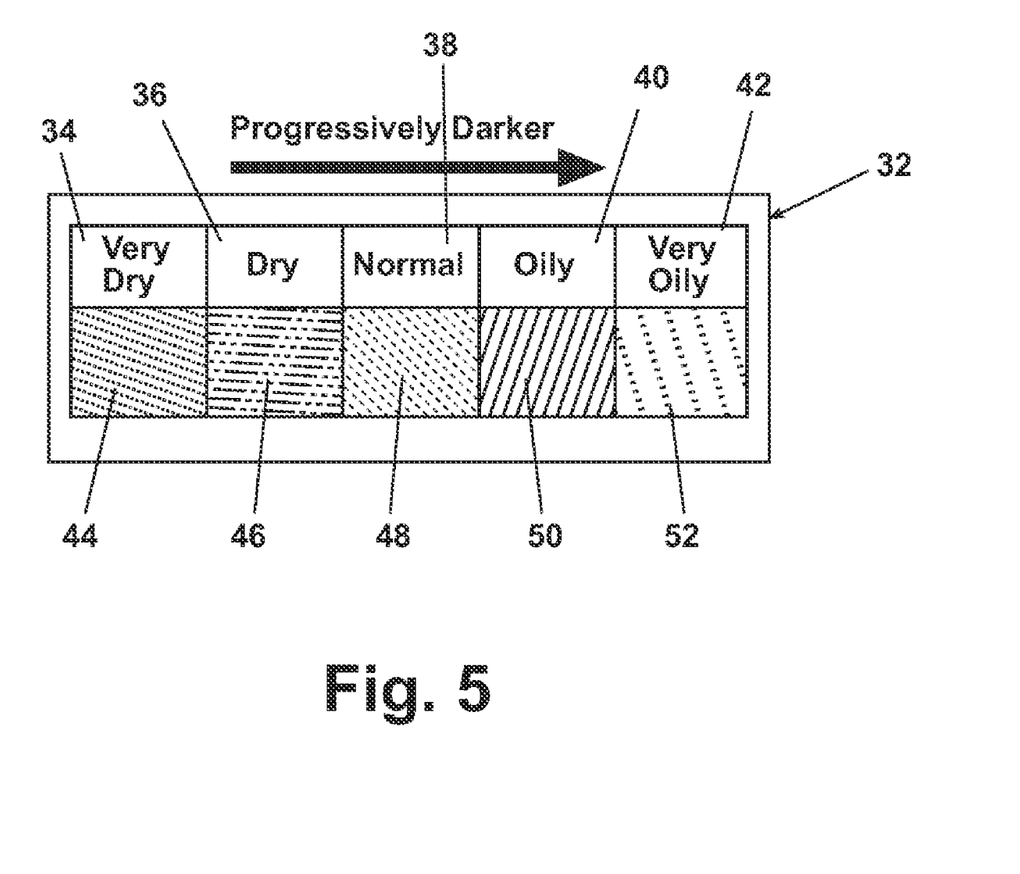
FIG. 5 is an example of a reference for characterization of skin condition, here a color chart that relates indicia to different skin conditions, for use with the indicator as shown in FIGS. 2-4.

The color chart 32 shown in FIG. 5 associates a very dry 34, a dry 36, a normal 38, an oily 40, and a very oily 42 skin condition with distinct colors 44, 46, 48, 50, and 52, respectively. The colors 44, 46, 48, 50, 52 can be shown as individual, separate colors, or a palette of a single color shown in progressively increasing intensity or "darkness". It will be understood that the categories 34-42 shown in the color chart 32 in FIG. 5 are by example only and it will be well understood that different categorizations of various skin conditions can be made without departing from the scope of this invention.

Figure 6:
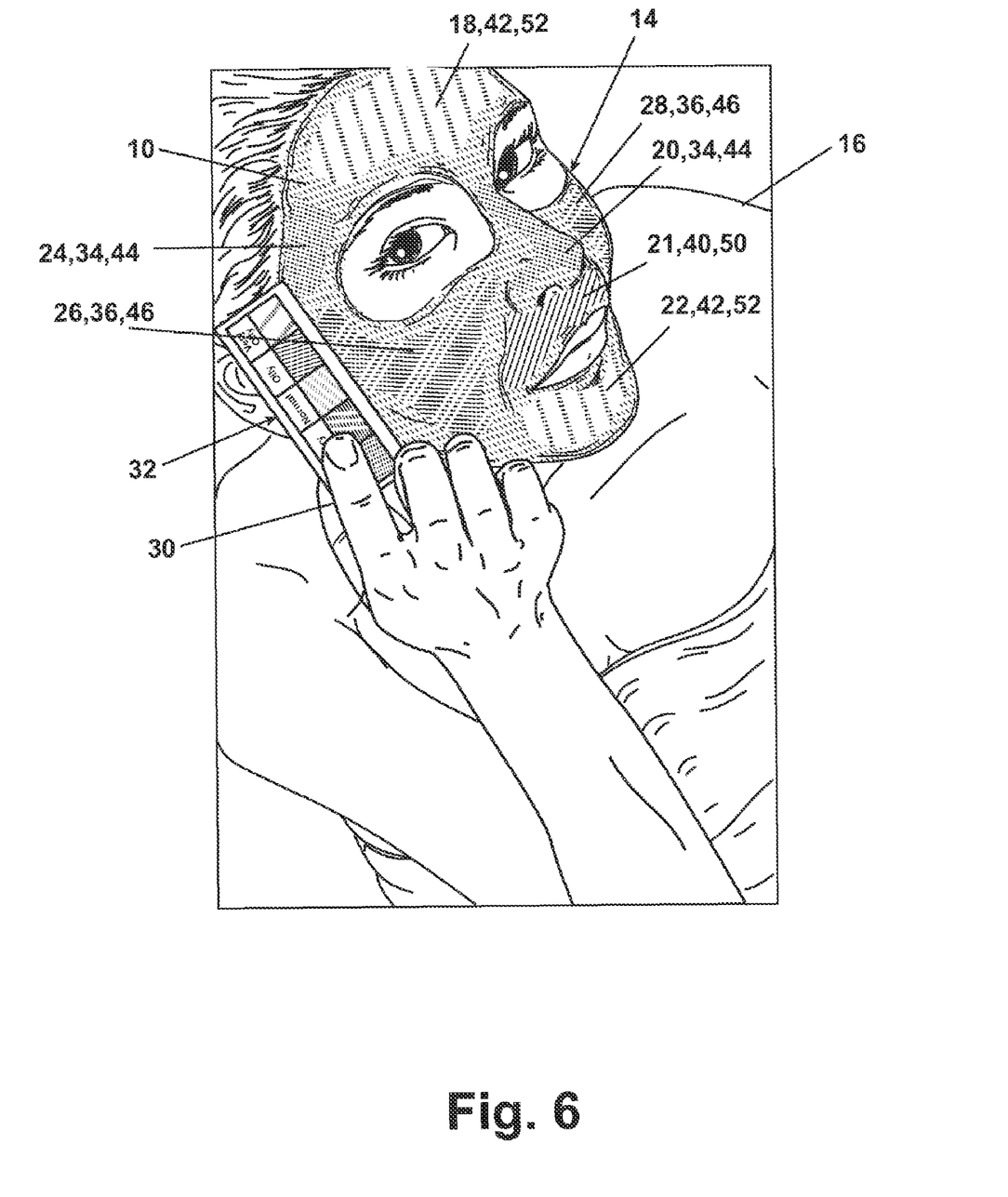
FIG. 6 is a perspective view of the user in FIG. 1 using the reference of FIG. 5 to determine skin condition in the various regions of the face.

Referring now to FIG. 6, the user 12 compares the indicator 10 to the reference, here the colors 44-52 on the color chart 32. Solely for exemplary purposes, the user 12 in FIG. 6 would characterize skin condition as follows: the forehead 18 and the chin 22 are very oily 42, the upper lip 21 is oily 40, the nose 20 and the temple 24 are very dry 34, the right cheek 26 and the left cheek 28 are dry 36, and the areas in between are normal 38. This evaluation is performed by matching the colors 44-52 on the color chart 32 with the colors shown in the activated indicator 10 and then reading the particular categorization of the matched colors with the indicated categories 34-42.

Figure 7:
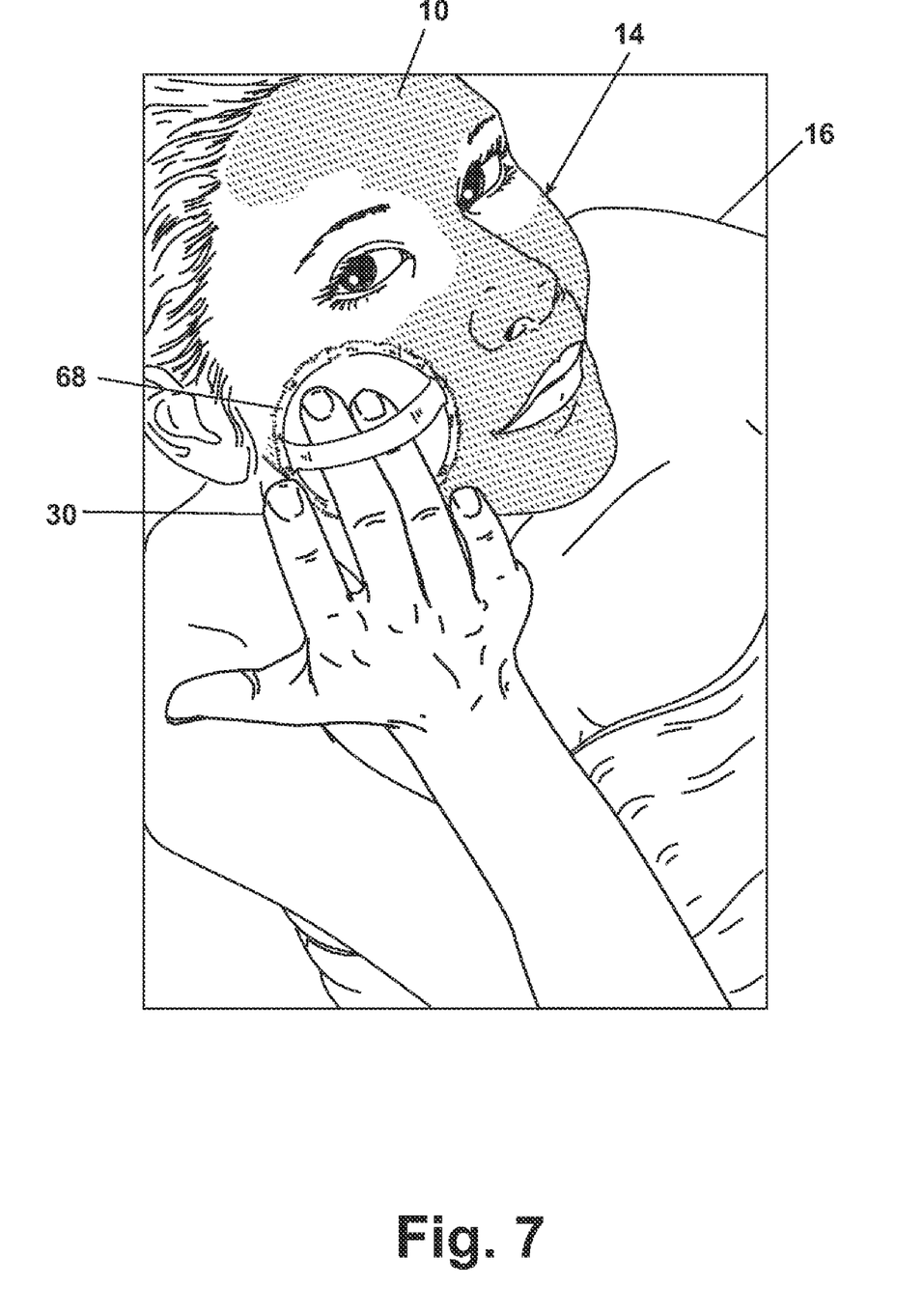
FIG. 7 is a perspective view similar to FIG. 2, wherein the user of FIG. 1 is applying a powder form of the indicator by an applicator.
Figure 7A:
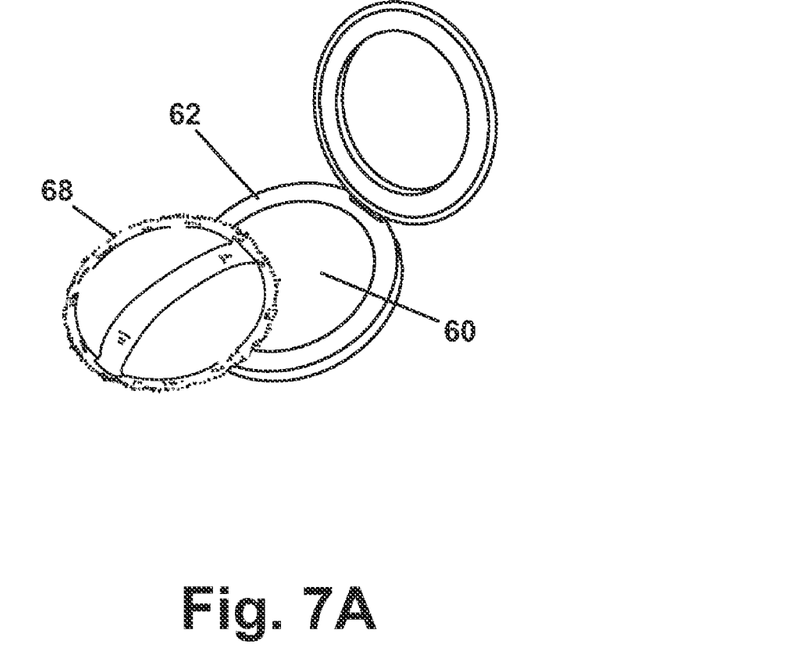
FIG. 7A is a perspective view of the indicator of FIG. 7, wherein the indicator is a pressed powder packaged in a compact.
Figure 7B:
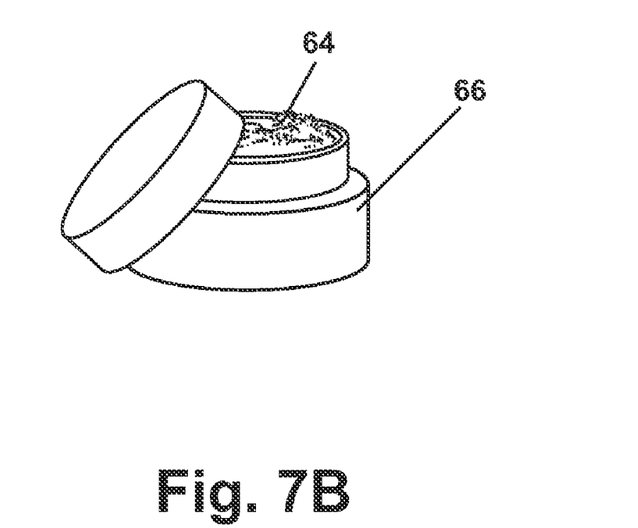
FIG. 7B is a perspective view of the indicator of FIG. 7, wherein the indicator is a loose powder packaged in a screw top container.

Other exemplary methods and devices for applying the indicator 10 to the skin include utilizing a conventional cosmetic applicator. When the indicator 10 is a powder form and packaged as, for example, a pressed powder 60 in a compact 62, as shown in FIG. 7A, or a loose powder 64 in a screw top container 66, as illustrated in FIG. 7B, the user 12 can employ a cosmetic applicator pad or puff 68, as shown in FIG. 7, or, alternatively, a brush, a sponge, or other suitable applicator to apply the indicator 10 to the desired areas. Such applicators advantageously avoid contact of the hand 30 with the indicator 10 and, therefore, prevent undesirable transfer of oils and other chemicals from the hand 30, which can potentially affect characterization of skin type. Additionally, the applicators can be washed prior to use of the indicator 10 to further prevent contamination thereby.

When the indicator 10 is a low viscosity fluid system, it can be packaged in a suitably sized retail container with a dispenser comprising, for example, a manual pump or an aerosol propellant. Alternatively, the indicator 10 could be administered through a device comprising spray nozzles or pressurized jets that evenly distribute or mist the indication system 10 over the desired areas of the user 12.

Other application methods and devices contemplated by the invention include a combined package and applicator that meters a predetermined amount of the indicator 10 in the proximity of the applicator, which is then utilized to apply to the predetermined amount of the indicator 10 to the desired areas of the user's body. By metering the indicator 10, the amount applied to the user 12 can be controlled to ensure that enough of the indicator 10 is present to be able to accurately characterize skin condition while avoiding excessive application, which is wasteful and can potentially affect the visual appearance of the activated indicator 10.

Figure 8:
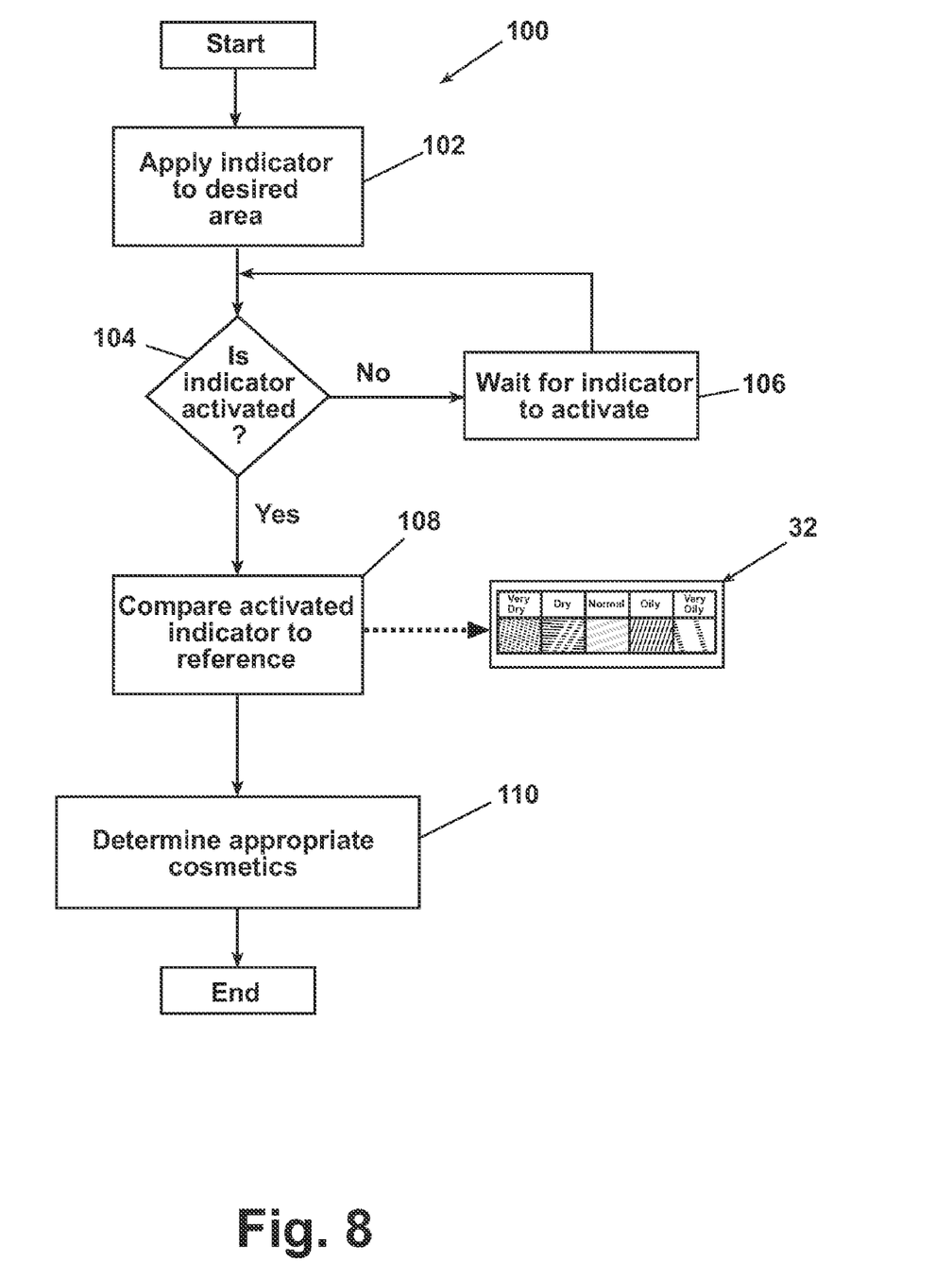
FIG. 8 is a flow chart explaining an exemplary method of using the indicator according to the invention to ultimately determine the user's skin condition for a purpose such as the user's personal selection of appropriate cosmetics.

Referring now to FIG. 8, the present invention also includes an exemplary method 100 for employing the indicator 10 that provides a visual indication of a user's skin condition. It will be understood that the reference numerals employed with the description of FIGS. 1-6 are also used with the description of the method of FIG. 8.

The particular steps of the example method 100 will now be described with reference to FIG. 8. It will be understood that the prior description of the use of the indicator 10 is incorporated herein by reference. First, the indicator 10 is applied to the desired area(s) of a user 12 <step 102>. Next, the user 12 determines whether the indicator 10 is activated <decision point 104>. If the indicator 10 is not yet activated, the user 12 waits for the indicator 10 to activate <106> and returns to decision point <104>. If the indicator 10 is activated, the user 12 then compares the indicator 10 to the reference 32, such as the color chart 32, to characterize skin condition <108>. Based on the results, the user 12 can optionally determine appropriate cosmetics, skin care products, and other beauty products 154 <110>.

The composition of the indicator 10 of the invention comprises one or more non-water soluble dyes, a flowable carrier, one or more optional opacifiers, and one or more optional additives. Several ingredients in these categories are suitable for use in the composition of the indicator 10, as will be known by those skilled in the art. Examples of each type of ingredient are provided below.

The non-water soluble dyes are preferably soluble in oil and, therefore, interact with the sebum and other oily substances in skin oil to provide a visual change indicative of skin condition. Preferably, the visual change in the at least one dye is proportional to the amount of oil present in solution. The visual change can be, for example, an appearance of color, wherein a color transitions from being substantially unperceivable to being detectable, or a change in intensity of a color. Any non-water soluble dyes approved currently and in the future by the United States Food and Drug Administration (FDA) are acceptable for use in the indicator 10. For example, oil soluble Drug and Cosmetics (D&C) colorants, which are approved by the FDA for use in cosmetics that come into contact with human skin, can be employed. Suitable D&C colorants include, but are not limited to, violet 2, yellow 11, and red 17. Dyes can be used independently or mixed together in order to create the desired color or colors. Further, concentrations and combinations of the dyes, or individual dyes, can be optimized for use on various skin tones and skin colors.

Figure 9:
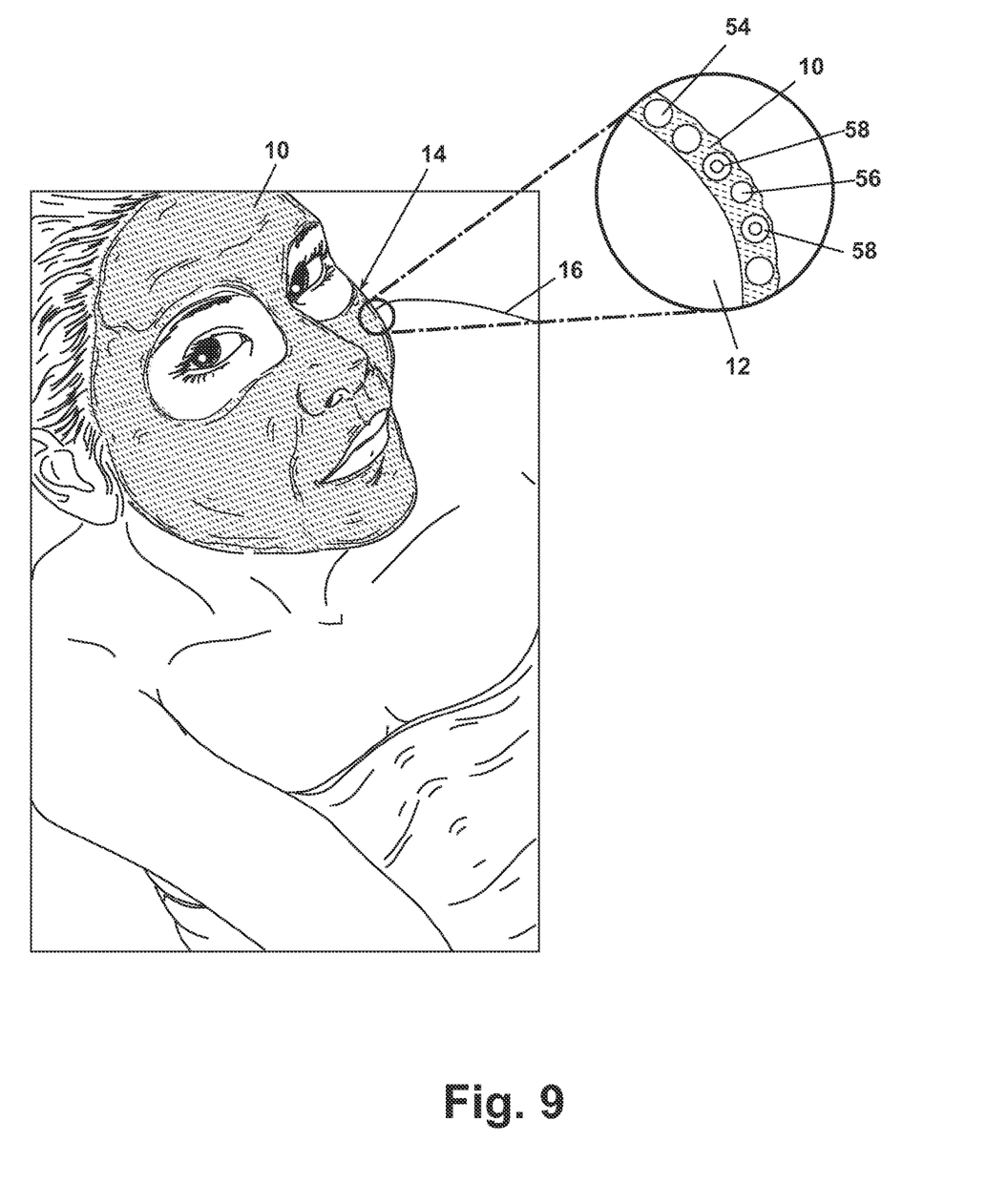
FIG. 9 is a perspective view of the user in FIG. 1 using an indicator according to the invention containing encapsulated dye(s) and an enlarged sectional view of the indicator containing the encapsulated dye(s).

Referring to FIG. 9, the one or more non-water soluble dyes can be provided optionally in encapsulated spheres 54, or other suitable encapsulated geometry, comprised of a material that degrades, dissolves, disintegrates, or is otherwise altered when in contact with a sufficient, predetermined amount of oil so that the sphere 54 opens and releases the previously encapsulated dye(s). The dye or combination of dyes can be encapsulated in spheres having a single layer of encapsulating material 56 or spheres having multiple layers of encapsulating material 58. Additionally, different encapsulating materials having distinct, known oil thresholds for dissolution, disintegration, or alteration can be employed. As a result, the copious possible combinations of dyes and layers and types of encapsulating materials not only provides numerous ways to manifest visual qualitative indications of various types of skin condition, but also facilitates a somewhat quantitative measure of skin oil levels.

The flowable carrier carries the non-water soluble dye and, in a fluid system, comprises water and one or more rheology modifiers, or in a powder system, excludes water and any rheology modifier. The rheology modifiers are blended with the water to alter the rheological properties, such as viscosity, of the indicator 10 so that the user 12 can apply the mask 10 to the skin areas in desirable manner. For example, the viscosity of the spreadable form is suitable for facile spreading of the indicator 10 over the desired areas. The rheology modifiers can be selected based on the desired type of the indicators 10, such as the indicators 10 that are removed by washing or the indicators 10 that are removed by peeling. Further, the relative concentrations of the rheology modifier and the water can be adjusted based on the type of indicator 10. There are copious rheology modifiers known to those skilled in the art, most of which are listed in the "International Cosmetic Ingredient Dictionary and Handbook," available from the Cosmetic, Toiletry, and Fragrance Association (CTFA), which is incorporated herein by reference. The rheology modifiers listed in the CTFA handbook and combinations thereof can be employed to create numerous formulations for the indicator 10 and adjust the viscosity of the indicator 10 for effective delivery of the one or more non-water soluble dyes to the surface of the skin.

For example, ceramic or polymer materials can be employed as rheology modifiers. When the indicator 10 employs a ceramic rheology modifier, the indicator 10 advantageously absorbs oil rapidly from the skin's surface, thus reducing activation time and providing an accurate representation of the quantity of oil present on various skin surfaces. The ceramic-based indicator 10 can incorporate water into the carrier for the spreadable form, which has a consistency similar to well-known clay cosmetic masks. Bentonite clay, which consists of the mineral montmorillonite, is an example of a suitable ceramic rheology modifier. There are many grades, or purities, of bentonite clay with different oil absorbing properties, and correspondingly, the grade used in the indicator 10 should relate to the desired level of oil absorbency. Other examples of ceramic rheology modifiers are sodium bentonite, such as Aquagel® (available from Baroid Industrial Products, Inc.), and magnesium aluminum silicate.

Examples of polymer-based indicators 10 are a gel form and a peelable form. The gel forms typically have a fluffy consistency, can be removed from the skin by simple washing, and preferably incorporate Carbopol® polymers (available from Noveon, Inc.), most of which are high molecular weight homo- and copolymers of acrylic acid crosslinked with a polyalkenyl polyether. The peelable forms are spread onto the skin in a liquid form and can be peeled therefrom after sufficiently solidifying or can removed from the skin with water. Optionally, the peelable form can be designed to provide a replica of the desired areas user's body and a map of the skin type(s) of the desired areas on the inner surface thereof. When the peelable form is activated and peeled from the user's body, the user 12 can simply look at the replica/map and compare it to the reference 32 to characterize the skin type(s). The peelable forms preferably incorporate polyvinyl alcohol (PVA) into the carrier. Other examples of polymer rheology modifiers are polyvinylpyrrolidone and methylethylcellulose, such as Natrosol® (manufactured by Aqualon, Inc.). The polymer rheology modifiers are not limited to use in the polymer-based indicator. For example, polyvinylpyrrolidone and methylethylcellulose can be utilized as rheology modifiers in ceramic-based indicators.

The flowable carrier in the powder form of the indicator 10 is preferably an agglomeration of finely dispersed solid particles that delivers, such as by adsorption, the non-water soluble dye to the surface of the skin. When applied to the skin, the powder form readily conforms to the contours of the user's body and provides excellent coverage of the desired areas. Further, because the power form is inherently applied in a thin layer, the activation of the indicator 10 occurs rapidly. In other words, because the activation of the indicator 10 initiates at the surface of the skin and progresses outward, the user 12 is able to visually observe the activation in a relatively short period of time. An exemplary carrier for the powder form is talc.

The optional opacifiers are added to enhance the opacity of the indicator 10 and hide the natural skin tone of the user 12 to provide a uniform, neutral background from which the visual indication can develop. Suitable opacifiers include, but are not limited to, talc, kaolin, titanium dioxide, magnesium carbonate, and calcium carbonate. Similar to the non-water soluble dyes, the opacifiers can be used independently or as a mixture to create the desired opacity.

The optional additives can be incorporated into the indicator 10 for various purposes. For example, the additives can adjust the pH of the indication system 10 to a desired level, and a suitable pH neutralizer is triethanolamine. Other additives can be utilized as preservatives, wetting agents, and humectants. An exemplary microbiological preservative is methyl paraben, and an exemplary wetting agent and humectant is glycerin. Further, the indicator 10 can include one or more solvents, such as isopropyl alcohol. Optionally, the additives can also function as a rheology modifier.

EXAMPLES

Exemplary compositions of a spreadable ceramic-based indicator 10, a powder indicator 10, a spreadable/peelable polymer-based indicator 10, and a spreadable gel polymer-based indicator 10 are presented in Tables 1-4, respectively.

TABLE 1

Spreadable Ceramic-Based Indicator

| INGREDIENT | CONCENTRATION (Weight %) |
|---|---|
| Water | 77.0 |
| Bentonite | 15.0 |
| Magnesium Aluminum Silicate | 0.75 |
| Titanium Dioxide | 4.0 |
| Glycerin | 2.0 |
| Dye | 1.0 |
| Methyl Paraben | 0.25 |

TABLE 2

Powder Ceramic-Based Indicator

| INGREDIENT | CONCENTRATION (Weight %) |
|---|---|
| Talc | 93.5 |
| Titanium Dioxide | 4.0 |
| Glycerin | 1.5 |
| Dye | 1.0 |

TABLE 3

Spreadable/Peelable Polymer-Based Indicator

| INGREDIENT | CONCENTRATION (Weight %) |
|---|---|
| Water | 52.75 |
| Isopropyl Alcohol | 24.0 |
| Polyvinyl Alcohol | 15.0 |
| Titanium Dioxide | 4.0 |
| Glycerin | 3.0 |
| Dye | 1.0 |
| Methyl Paraben | 0.25 |

TABLE 4

Spreadable Gel Polymer-Based Indicator

| INGREDIENT | CONCENTRATION (Weight %) |
| --- | --- |
| Water | 91.00 |
| Carbopol 940 | 1.00 |
| Triethanolamine | 0.75 |
| Titanium Dioxide | 4.00 |
| Glycerin | 2.00 |
| Dye | 1.00 |
| Methyl Paraben | 0.25 |

While particular embodiments of the invention have been shown, it will be understood, of course, that the invention is not limited thereto since modifications may be made by those skilled in the art, particularly in light of the foregoing teachings. Reasonable variation and modification are possible within the scope of the foregoing disclosure of the invention without departing from the spirit of the invention.

What is claimed is:

1. A system for characterizing skin condition, the system comprising:
   a spreadable indicator suitable for application to human skin, the indicator being reactive to at least one substance secreted by human skin so that the spreadable indicator visually changes color or color intensity in response to reacting with the at least one substance, wherein a degree of visual change of color or color intensity of the indicator is representative of the amount of oil in contact with the indicator; and
   a reference relating a plurality of possible visual changes of color or color intensity of the indicator to a plurality of skin conditions so as to enable a comparison of the reference to the visual change of the indicator to characterize a skin condition of human skin due to the amount of the oil in contact with the indicator,
   wherein the indicator comprises at least one dye soluble with oil found on human skin to effect the visual change of the indicator and
   wherein the at least one dye comprises at least one Drug and Cosmetics colorant from the group consisting of violet 2, yellow 11, and red 17.

2. The system of claim 1 wherein the spreadable indicator is a facial mask.

3. The system of claim 2 wherein the facial mask is a clay-based mask.

4. The system of claim 2 wherein the facial mask is a polymer-based mask.

5. The system of claim 1 wherein the spreadable indicator is a gel.

6. The system of claim 1 wherein the spreadable indicator is a powder.

7. The system of claim 1 wherein the reference comprises indicia representative of the plurality of possible visual changes of the indicator.

8. The system of claim 1 wherein the indicia comprises a color chart.

9. The system of claim 1, wherein the reference assists in selecting cosmetics appropriate for the characterized skin condition.

10. The system of claim 1 wherein the indicator is in the form of a pressed powder.

11. The system of claim 1 wherein the indicator is in the form of a loose powder.

12. The system of claim 1, further comprising an applicator configured to apply the indicator to the human skin.

13. The system of claim 12 wherein the applicator comprises at least one of a sponge, a pad, a puff, and a brush.

* * * * *